United States Patent
Shimoda et al.

(10) Patent No.: US 12,194,074 B2
(45) Date of Patent: Jan. 14, 2025

(54) METHOD OF REDUCING MUSCLE DAMAGE ASSOCIATED WITH INTENSIVE EXERCISE BY ADMINISTERING PURPLE-TEA EXTRACT

(71) Applicant: ORYZA OIL & FAT CHEMICAL CO., LTD., Aichi (JP)

(72) Inventors: Hiroshi Shimoda, Aichi (JP); Hiromichi Murai, Aichi (JP)

(73) Assignee: ORYZA OIL & FAT CHEMICAL CO., LTD., Aichi (JP)

( * ) Notice: Subject to any disclaimer, the term of this patent is extended or adjusted under 35 U.S.C. 154(b) by 56 days.

(21) Appl. No.: 18/107,544

(22) Filed: Feb. 9, 2023

(65) Prior Publication Data

US 2023/0190854 A1 Jun. 22, 2023

Related U.S. Application Data

(62) Division of application No. 17/143,375, filed on Jan. 7, 2021, now abandoned.

(30) Foreign Application Priority Data

Jan. 29, 2020 (JP) ................. 2020-012366
Apr. 2, 2020 (JP) ................. 2020-066863

(51) Int. Cl.
*A61K 36/82* (2006.01)
*A61K 31/7032* (2006.01)
*A61P 21/00* (2006.01)

(52) U.S. Cl.
CPC .......... *A61K 36/82* (2013.01); *A61K 31/7032* (2013.01); *A61P 21/00* (2018.01)

(58) Field of Classification Search
None
See application file for complete search history.

(56) References Cited

U.S. PATENT DOCUMENTS

2019/0343858 A1 11/2019 Shimoda

FOREIGN PATENT DOCUMENTS

| JP | 2011-173817 | 9/2011 |
| JP | 2014-001163 | 1/2014 |
| WO | 2018/138929 | 8/2018 |

OTHER PUBLICATIONS

Kerksick, C.M., et al., Intramuscular adaptations to eccentric exercise and antioxidant supplementation, Amino Acids (2010) 39:219-232 (Year: 2010).*
Chavez, M.D., et al., "Impact of Superoxide Dismutase on Nitric Oxide and Peroxynitrite Levels in the Microcirculation—A Computational Model", Proceedings of the $29^{th}$ Annual International Conference of the IEEE EMBS Cite Internationale, Lyone, France Aug. 23-26, 2007.
Fukuda, T., et al., "Antioxidative polyphenols from walnuts" (*Juglans regia* L.), Phytochemistry 63 (2003) 795-801.
Gao, D-F., et a., "Phenolic Antioxidants from Green Tea Produced from Camellia taliensis", J. Agric. Food Chem., 2008, 56, 7517-7521.

* cited by examiner

*Primary Examiner* — H. Sarah Park
(74) *Attorney, Agent, or Firm* — Bauer & Joseph

(57) ABSTRACT

A method of reducing muscle damage in a human being includes providing an extract of Kenyan purple tea (scientific name: *Camellia sinensis*; variety name: TRFK306) containing 1,2-di-O-galloyl-4,6-O—(S)-hexahydroxydiphenoyl-β-D-glucose (GHG). Then, an effective amount of the purple tea extract is administered to a body of a human being engaged in intensive exercise to reduce muscle damage associated with the intensive exercise.

2 Claims, 2 Drawing Sheets

Both Set 1 and Set 2 include benchpresses and leg extensions.

METHOD OF REDUCING MUSCLE DAMAGE ASSOCIATED WITH INTENSIVE EXERCISE BY ADMINISTERING PURPLE-TEA EXTRACT

TECHNICAL FIELD

This invention relates to a NO (nitric oxide, also called nitrogen monoxide) production promoter and is widely used in foods, pharmaceuticals, cosmetics and the like.

TECHNICAL BACKGROUND

NO (nitric oxide, also called nitrogen monoxide) is produced when L-arginine is oxidized to L-citrulline, and the reaction is catalyzed by NO synthase (NOS). NO production is observed in various tissues and cell species in a living organism, and a typical cell species that constantly produces and releases NO is a vascular endothelial cell. It has been reported that NO (vascular endothelial NO) produced in vascular endothelial cells is an endothelium-derived vascular relaxation factor (EDRF) (see Non-Patent Documents 1 and 2). Therefore, compounds that promote spontaneous and sufficient NO production in vascular endothelial cells, and compounds that have an eNOS-activating effect, improve vascular endothelial function and are thus considered to be an excellent therapeutic agent for impaired blood flow, arteriosclerosis, hyperlipidemia, ischemic cardiac diseases or other diseases caused by vascular endothelial dysfunction such as circulatory failure in various organs. Therefore, conventionally, searches for a compound having a NO-production-promoting action have been conducted, and various NO-production-promoting agents have been proposed (Patent Document 1). Further, it is known that enhancing the NO-production-promoting action improves male function (Patent Document 2). In addition, NO production is known to be involved in improving exercise performance. For example, it is reported that the amount of exercise decreases when NO production is blocked by L-NAME (Non-Patent Document 9), and that NO production improves the griping-strength of aged mice and lessens inflammation of skeletal muscles (Non-Patent Document 10).

On the other hand, due to the so-called muscle training boom in recent years, the demand for supplements (Non-Patent Document 3) with muscle maintenance after a workout as a health claim is increasing. As an example, it has been reported that beet juice containing nitric oxide (NO) exhibits a muscle maintenance effect through vasodilatory action (Non-Patent Document 4).

There are various clinical effects on post-exercise muscle recovery in connection with polyphenols having NO-producing effects. For example, cocoa flavonoids lower ROS concentration in blood but do not affect NO-production (Non-Patent Document 5). Pomegranate polyphenols (gallotannins) increase oxygen-uptake quantity (VO2) but do not improve exercise (cycling) performance (Non-Patent Document 6). Also, resveratrol, which is known to suppress arteriosclerosis, also has a weak recovery effect after a workout. 19) Furthermore, it has been reported that blackcurrant containing a large amount of anthocyanins does not improve oxygen-uptake quantity (VO2) but increases cardiac output (Patent Document 8). In this way, even when the same term "polyphenol" is used, we can see that there are differences in the recovery effect after a workout, depending on the person.

Patent Document 1: Japanese Published Unexamined Patent Application No. 2014-001163
Patent Document 2: Japanese Published Unexamined Patent Application No. 2011-173817
Non-Patent Document 1: Nature, 1987, 327, 524-526
Non-Patent Document 2: Proc. Natl. Acad. Sci. USA, 1987, 84, 9265-9269
Non-Patent Document 3: Martin J. S. et al. J. Int. Soc. Sports Nutr. 14, 38 (2017)
Non-Patent Document 4: Richard J. C. et al. Physiological Rep. 6, e1352 (2018)
Non-Patent Document 5: Decroix L, et al. J. Int. Soc. Sports Nutr. 14:28 (2017)
Non-Patent Document 6: Crum E M, et al. J. Int. Soc. Sports Nutr. 14:14 (2017)
Non-Patent Document 7: Gliemann L. et al. Free Radic. Biol. Med. 98,165-176 (2016)
Non-Patent Document 8: Willems M E, et al, Int. J. Sport. Nutr. Exerc. Metab. 25,367-374 (2015).
Non-Patent Document 9: Basic Res. Cardiol. 2017 Sep. 8; 112 (6): 59.
Non-Patent Document 10: Nitric Oxide. 2018 Nov. 1; 80: 70-81.

DISCLOSURE OF THE INVENTION

Problems to be Solved by the Invention

Under such circumstances, the present inventor learned that purple tea and its inherent component 1,2-di-O-galloyl-4,6-O—(S)-hexahydroxydiphenoyl-β-D-glucose has a NO-production-promoting effect, and then he completed this invention. It was also found that purple-tea extract has the effect of improving the performance of muscles of the lower extremity at the start of training, which requires instantaneous power. At that time, it was also found that purple-tea extract has the effect of reducing muscle damage associated with intensive exercise, and then this invention was completed. That is, the objective of this invention is to provide a novel NO-production promoter, an enhancer of instantaneous force in the muscles of the lower extremity using the promoter, and a reducer of muscle damage associated with intensive exercise.

Means for Solving the Problems

The technical features of this invention for solving the above problems are as follows.
1. A NO-production promoter containing 1,2-di-O-galloyl-4,6-O—(S)-hexahydroxydiphenoyl-β-D-glucose as the active ingredient.
2. A NO-production promoter containing a composition containing 1,2-di-O-galloyl-4,6-O—(S)-hexahydroxydiphenoyl-β-D-glucose as the active ingredient.
3. A NO-production promoter containing a GHG-containing composition derived from Kenyan purple tea (scientific name: *Camellia sinensis*; variety name: TRFK306) as the active ingredient.
4. An enhancer of instantaneous force in the muscles of the lower extremity, which contains an extract of Kenyan purple tea (scientific name: *Camellia sinensis*; variety name: TRFK306) as the active ingredient.
5. A reducer of muscle damage associated with intensive exercise, which contains an extract of Kenyan purple tea (scientific name: *Camellia sinensis*; variety name: TRFK306) as the active ingredient.
6. A method of promoting NO-production in a human being, comprising:

a) providing an extract of Kenyan purple tea (scientific name: *Camellia sinensis*; variety name: TRFK306) containing 1,2-di-O-galloyl-4,6-O—(S)-hexahydroxy-diphenoyl-β-D-glucose (hereinafter referred to as GHG); and (b) administering an effective amount of the purple-tea extract to a body of a human being in need of NO-production promotion.

7. A method of promoting NO-production in a human being according to the above 6th aspect of this invention, wherein the Kenyan purple tea extract contains 3 to 10% by mass of GHG.

8. A method for improving muscle-instantaneous force in lower extremity muscles of human beings, comprising:

a) providing an extract of Kenyan purple tea (scientific name: *Camellia sinensis*; variety name: TRFK306) containing 1,2-di-O-galloyl-4,6-O—(S)-hexahydroxy-dipherioyl-β-D-glucose (hereinafter referred to as GHG); and (b) administering an effective amount of the purple-tea extract to a human being (at least prior to the human being engaging in lower extremity exercises) to improve the instantaneous force in the lower-extremity muscles of the human being.

9. A method for improving muscle-instantaneous force in lower extremity muscles of human beings according to the above 8th aspect, wherein the Kenyan purple tea extract contains 3 to 10% by mass of GHG.

10. A method for reducing muscle damage in a human being, comprising:

a) providing an extract of Kenyan purple tea (scientific name: *Camellia sinensis*; variety name: TRFK306) containing 1,2-di-O-galloyl-4,6-O—(S)-hexahydroxy-diphenoyl-β-D-glucose (hereinafter referred to as GHG); and (b) administering an effective amount of the purple-tea extract to a human being at least prior to the human being engaging in intensive exercises to reduce muscle damage associated with the intensive exercise of the human being.

11. A method for reducing muscle damage in a human being according to the above 10th aspect of this invention, wherein the Kenyan purple tea extract contains 3 to 10% by mass of GHG.

MODES FOR CARRYING OUT THE INVENTION

Figure 1:
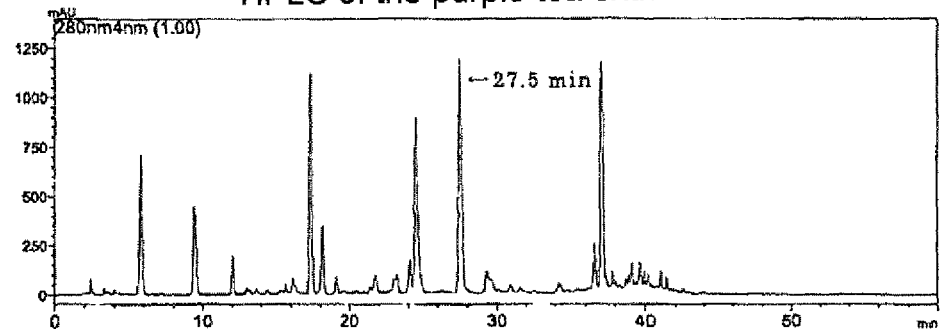
FIG. 1 is an HPLC chromatogram of the Kenyan purple-tea extract (purple-tea extract) as an example of this invention.

Hereinafter, this invention is described in detail.

The NO-production promoter of this invention is characterized in comprising 1,2-di-O-galloyl-4,6-O—(S)-hexahydroxydiphenoyl-β-D-glucose (hereinafter referred to as "GHG") as the active ingredient. GHG is represented by the following chemical formula (1).

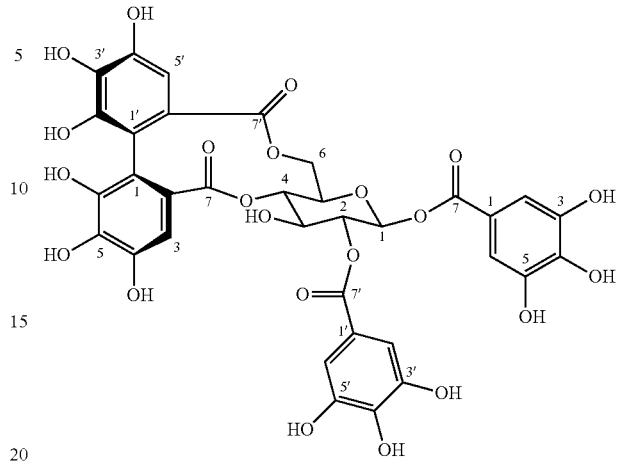

Chemical Formula 1

The NO-production promoter of this invention has a GHG-containing composition as an active ingredient. As for the GHG-containing composition, it is preferable to use one derived from Kenyan purple tea (scientific name: *Camellia sinensis*; variety name: TRFK306). The GHG-containing composition is an extract obtained from Kenyan purple tea, and contains GHG in the content of 3 to 99% by mass. The shape may be liquid, solid, semi-solid or gel or the like, and the solid-converted content of the GHG is preferably 3 to 99% by mass. However, if it is used as a material for foods, drinks and cosmetics, the solid-converted content is preferably 3 to 30% by mass, more preferably 3 to 10% by mass, thus improving its productivity. In particular, a GHG-containing composition, containing GHG in content of 3 to 10% by mass, can be efficiently obtained by the production method as described below.

Kenyan purple tea, which is to be the raw material of the GHG-containing composition, is a tea plant that the Kenyan government developed by crossbreeding, and its variety name is now TRFK306. The tea leaves of Kenyan purple tea contains anthocyanins, and the color is purple. Therefore, it is commonly called "purple tea." In addition to TRFK306, there are other known purple teas such as Sun Rouge developed by an agricultural research institute (The National Agriculture and Food Research Organization), but Kenyan purple tea contains a highly-concentrated and specific component of GHG that does not exist in other purple teas.

The part of Kenyan purple tea (hereinafter simply referred to as "purple tea") that is used for producing the GHG-containing composition is not particularly limited, and leaves, stems, roots, flowers, seeds and the like can also be used. In particular, it is preferable to use the leaves, since a higher concentration of GHG can be obtained therefrom.

The GHG-containing composition of this invention preferably can be derived by crushing e.g. the fresh or dried leaves of Kenyan purple tea (hereinafter called purple-tea leaves) and then deriving the GHG-containing composition from such fresh or dried leaves by using a polar solvent (with water). Hereinafter the same shall apply. However, the GHG-content extract can be more efficiently extracted by chemically treating the purple-tea leaves with an acid or an alkaline decomposition or an enzyme decomposition or the like.

Specifically, the GHG-containing composition can be produced by the method described below. That is, firstly, the purple-tea leaves, either raw or dried, are subjected to a chemical treatment using acid or an alkali decomposition, an enzymatic decomposition or the like.

Then, a polar solvent is added to the purple-tea leaves, and such mixture of solvent and purple-tea leaves is shaken or heated under reflux to extract the GHG from the purple-tea leaves.

At this time, not only a polar solvent can be used but also water, alcohol or ketone. Also, a mixture of one or more of these solvents can be used. In addition, it is preferable to use either aqueous alcohol or aqueous ketone.

As a hydroalcohol-based solvent, a hydrous solvent such as ethanol, methanol, propanol or the like can be used. Hydrous ethanol is particularly preferable. Furthermore, as a hydrous ketone-based solvent, a hydrous solvent such as acetone, methyl-ethyl ketone, diethyl ketone or chloroacetone can be used. Hydrous acetone is particularly preferable.

In the case of hydrous ethanol, the ethanol content is 1 to 99.9% by mass, preferably 30 to 99% by mass, more preferably 40 to 80% by mass, and most preferably 40 to 60% by mass. In the case of hydrous acetone, it is preferable that it contains 20 to 99.9% by mass of acetone. This is because the above range is excellent in GHG-extraction efficiency. Hereinafter, for the convenience of representing the water-content ratio of the water-containing solvent, 80% by mass of ethanol hydrated, with 20% by mass of water, for example, is referred to as "80% hydrous ethanol."

As a method for producing the GHG-containing composition, heating and refluxing can be done by the well-known method of using a hydrous alcohol-based solvent or a hydrous ketone based solvent. The heating temperature is preferably about 30 to 95° C., more preferably about 30 to 50° C., and the refluxing time is preferably about one to four hours.

Also, in the method for producing the GHG-containing composition, shaking, stirring or the like can be done accordingly, as necessary.

Furthermore, in the method for producing the GHG-containing composition, it is preferable to distill the solvent under reduced pressure after extraction. As such, it is possible to prepare a composition that does not contain an organic solvent. This process can be applied to a food material to be blended in drinks and in foods such as functional foods, health foods or the like, thus making it possible to meet safety standards or the like.

Furthermore, in the method for producing the GHG-containing composition, a stepwise extraction can be done with a plurality of solvents. Thereby, the GHG-containing composition, containing a high concentration of OHO, can be produced in a higher yield.

Specifically, for example, the purple-tea leaves are added either to the above-mentioned hydroalcohol-based solvent or to the above-mentioned hydrous ketone-based solvent and then shaken or heated and fluxed to extract the GHG into the solvent, thus obtaining the first extract. The extract, and the residue that is not recovered as the extract, are separated by centrifugation or the like, and then the other of the above solvents that had not been selected are added to the residue and shaken or heated and refluxed to extract the GHG into these solvents, thus obtaining the second extract. Then, the first extract and the second extract are mixed. Needless to say, this second extract can be used alone as the extract of the purple-tea leaves (the GHG-containing composition).

As such, by performing the stepwise extraction with a plurality of solvents, the purple-tea leaves are subjected to the first-extraction treatment using the hydrous alcohol-based solvent or the hydrous ketone-based solvent, so that characteristics such as the physical properties of the purple-tea leaves are extracted to be changed preferably for the extraction. Therefore, in the subsequent second-extraction treatment, it is expected that the extraction efficiency will have been improved, not only when the hydrous alcohol-based solvent or hydrous ketone-based solvent is used but also when other solvents are used.

The extract, obtained by the above method of extraction, can be used as it is or concentrated to obtain the GHG-containing composition. Further, the extract can be powdered by freeze-drying or spray-drying to obtain a powdery composition as the GHG-containing composition. However, such a GHG-content extract is not limited to just that condition. Insoluble matter within the extract can be removed accordingly by filtering such extract or the like, or such insoluble matter can be crushed into microscopic particles.

As a method for producing the GHG of this invention, it is preferable to fractionate and distillate the GHG-containing composition that was obtained by the above process, based on the index that is the already-known GHG, by using an ion-exchange process, a size-exclusion chromatography process, a High-performance Liquid Chromatography (HPLC) process, a gel-filtration process or a membrane-separation process or the like. Of course, it is possible to extract and distillate the GHG from a material other than Kenyan purple tea. Also, it is possible accordingly to use an organic-synthetic method.

The NO-production promoter of this invention can be shaped into a drug or quasi-drugs such as tablets, granules, powdered medicines, liquids, powders, capsules, jellies or the like by adding base materials and carriers to the GHG or to the GHG-containing composition as the active ingredient.

Also, the GHG or GHG-containing composition as the active ingredient of this invention can be used as an element in various foods, drinks and cosmetics. These components mean materials obtained technically by mixing the ingredients that are appropriate for various uses.

Examples of this invention regarding foods and drinks include e.g. edible oils (salad oils), confectionary (chewing gums, candies, caramels, chocolates, cookies, snacks, jellies, gummies, tablet-shaped sweets, or the like), noodles (Japanese buckwheat noodles called Soba, Japanese wheat noodles called Udon, Japanese noodles called Ramen, or the like), dairy food (milk, ice cream, yogurt, or the like), seasoning (fermented rice, barley, soybean paste or the like called Miso, soy sauce called Shoyu, or the like), soups, drinks (juice, coffee, black tea, green tea, carbonated drink, sports supplement drinks, or the like) including general foods and healthy foods (tablet types or capsule types, or the like) and nutritional supplements (nutritious supplement drinks, or the like). The GHG or GHG-containing composition can be added accordingly to the above foods and drinks.

According to the type of food and drink elements, the following ingredients can be added: glucose, fructose, sucrose, maltose, sorbitol, stevioside, corn syrup, lactose, citric acid, tartaric acid, malic acid, succinic acid, lactic acid, L-ascorbic acid, dl-α-tocopherol, sodium erythorbate, glycerin, propylene glycol, glycerin fatty-acid ester, polyglycerol fatty-acid ester, sucrose fatty-acid ester, sorbitan fatty-acid ester, propylene glycol fatty-acid ester, Gum arabic, carrageenan, casein, gelatin, pectin, agar-agar (gelatin made from seaweed), the vitamin B family, nicotinic-acid amide, pantothenate acid calcium, amino acids, calcium salts, pigment, aroma chemicals or preservatives, or the like.

Furthermore, of the food composition and beverage composition with a health maintenance function, it is possible to blend the agents such as other antioxidants and health food materials, e.g. antioxidants, reduced ascorbic acid (vitamin C), vitamin E, reduced glutatin, tocotrienol, vitamin A derivative, lycopene, beta-cryptoxanthin, astaxanthin, zeaxanthin, fucoxanthin, uric acid, ubiquinone, Coenzyme Q10, folic acid, garlic extract, alicine, sezamine, lignans, catechin, isoflavone, chalcon, tannins, flavonoids, coumarin, isokmarins, blueberry extract, albutin, tannin, anthocyanins, apple polyphenol, grape seed extract, elladic acid, kojic acid, surge extract, V. (vitamin) A, V.B1, V.B2, V.B6, V.B12, V.C, V.D, V.E, V.P, choline, niacin, pantothenic acid, calcium folic acid, EPA, oligosaccharides, dietary fiber, squalene, soybean lecithin, taurine, donaliela, protein, octacosanol, DHA, egg yolk lecithin, linoleic acid, lactoferrin, magnesium, zinc, chromium, selenium, potassium, heme iron, oyster meat extract, chitosan, chitin oligosaccharide, collagen, chondroitin, turmeric, sweetroot, Lycium chinese fruit, cinnamon cassia, hawthorn, ginger, bracket fungus, corbicula extract, chinese soft-shell turtle, plantain, chamomile, dandelion, hibiscus, honey, boren, royal jelly, lime, lavender, rosehip, rosemary, sage, bifidobacteria, facaris, *Bacillus coagulans* SANK 70258, wheat germ oil, sesame oil, perilla oil, soybean oil, medium chain fatty acids, agaricus, ginkgo leaf extract, turmeric, chondroitin, brown rice germ extract, lychee, onion, DHA, EPA, DPA, Tencha tea, *Ophiocordyceps sinensis*, garlic, wasp larva, papaya, puerh tea, propolis, *Acer maximowiczianum, Hericium erinaceum*, Royal jelly, saw palmetto, hyaluronic acid, collagen, gaba, harp seal oil, shark cartilage, glucosamine, lecithin, phosphatidylserine, *Panax notoginseng*, mulberry leaves, soybean extract, echinacea, *Acanthopanax senticosus* Harms, barley extract, olive leaf, olive fruit, gymnema, *Lagerstroemia speciosa*, salacia, garcinia, chitosan, St. John's wort, Chinese date, carrot, passion flower, broccoli, placenta, adlay, grape seed, peanut testa, bilberry, black cohosh, milk thistle (*Silybum marianum*), laurel, sage, rosemary, *Apocynum venetum*, black vinegar, bitter gourd, maca, safflower, flax, oolong tea, flower thorn, caffeine, capsaicin, xylooligosaccharide, glucosamine, buckwheat, citrus, dietary fiber, protein, prune, spirulina, barley young leaf, nucleic acid, yeast, shiitake mushroom, plum meat, amino acid, deep-sea shark extract, noni, oyster meat, Chinese softshell turtle (terrapin), champignon, plantain, acerola, pineapple, banana, peach, apricot, melon, strawberry, raspberry, orange, fucoidan, Fomes yucatensis, cranberry, chondroitin sulfate, zinc, iron, ceramide, silk peptides, glycine, niacin, chastetree, ceramide, L-cysteine, L-carnitine, red wine leaves, millet, horsetail, biotin, centela asiatica, *Lonicera caerulea L. pycnogenol*, Japanese butterbur, rhubarb, clove, rosemary, catechin, puerh tea, citric acid, beer yeast, melilot, black ginger, ginger, zedoaria, nattokinase, monascuc, tocotrienol, lactoferrin, cinnamon, tartary buckwheat, cocoa, yuzu (Japanese citrus) seed extract, perilla fruit extract, lychee seed extract, evening primrose extract, black rice extract, alpha-lipoic acid, gaba, green coffee bean extract, Japanese butterbur extract, kiwi seed extract, Unshu citrus extract, red ginger extract, astaxanthin.

As a more specific method, spray-dry or freeze-dry the active ingredient of this invention i.e. the GHG or GHG-containing composition. Especially, in the case of the GHG-content extract, spray-dry or freeze-dry it with dextrin powder, thus making such extract into a powder, a granule, a tablet or a liquid to mix it easily with foods (instant food or the like). Also, it is possible, accordingly, to mix such extract with a binder such as gum Arabic or the like to make it into a powder or a granule, thus making it possible in adding it to solid food.

In the case that the NO-production promoter of this invention is formed into a pharmaceutical (including pharmaceuticals and quasi-drugs medicines), the active ingredients (GHG or GHG-containing composition) of this invention can be aptly mixed with raw materials to form the pharmaceuticals. Such pharmaceuticals can be used for humans and other organisms (mammalians or the like). The raw materials to be mixed with the above pharmaceuticals include e.g. vehicles (glucose, lactose, sucrose, sodium chloride, starch, calcium carbonate, kaolin, crystalline cellulose, cacao oil, hydrogenated vegetable oil, talc, or the like), binders (distilled water, normal saline solution, ethanolic solution, simple syrup, glucose solution, starch solution, gelatin solution, carboxymethyl cellulose, potassium phosphate, polyvinyl pyrrolidone, or the like), disintegrating agent (sodium alginate, agar-agar, sodium-hydrogen carbonate, calcium carbonate, sodium-lauryl sulphate, monoglyceride stearate, starch, lactose, gum arabic powder, gelatin, ethanol, or the like), disintegration-suppressive agent (sucrose, stearin, cacao oil, hydrogenated oil, or the like), absorption promoters (quaternary-ammonium base, sodium lauryl sulphate, or the like), adsorbents (glycerin, starch, lactose, kaolin, bentonite, silica acid, or the like), lubricant agents (purified talc, stearate, polyethylene glycol, or the like)

As a method for administering the above medicines, it is possible to administer them orally in the form of tablets, pills, soft or hard capsules, subtle granules, powders, granules, or the like. Water-soluble preparations can either be orally administered in liquid form or be parenterally administered after having dispersed them into a solubilizer such as ethanol, water, or the like, or into the different forms of a medical skin-patch, or into a lotion, an ointment, a tincture, a cream, or the like. Also, the water-soluble prepared medicines can simply be used or mixed with a dispersant, a suspension agent, a stabilizer, or the like, thus making it possible to use such preparations (prepared medicines) in the form of a medical skin patch, a lotion, an ointment, a tincture, a cream, or the like.

The applied dose can be adjusted according to the method of administration, to the condition of the disease, or to the age of the patient, or the like. Adults normally can take approx. 5.0 to 200 mg of an active ingredient per day; children can take 0.5 to 100 mg per day.

The blending ratio of the active ingredient (i.e. the GHG or GHG-containing composition) of this invention can be adjusted according to the way in which the medicine is to be administered. When such active ingredient is to be orally or mucosally administered, the applied dose should preferably be about 0.01 to 10.0 wt %. When it is to be parenterally administered, the dose should preferably be 0.01 to 20 wt %. The dose varies depending on the condition of the patient, so that a dose less than the above amount may be sufficient, or a greater amount may sometimes be needed. Medicinal elements possibly contain other ingredients such as the already-known ingredients that are regularly used in the pharmaceutical field and those ingredients necessary to make the active ingredient into any suitable form to be orally applied, including e.g. lactose, starch, hydroxypropylcellulose, kaolin, talc, calcium carbonate, or the like. Also, Sildenafil and its derivatives can be appropriately mixed."

Further, this invention can be applied to cosmetics. Forms of the cosmetic elements of this invention include e.g. emulsions, soaps, facial cleansers, bath agents, creams, skin lotions, colognes, shaving creams, shaving lotion, beauty oils, sunscreen lotions, face powders, foundations, perfumes, facial masks, nail creams, nail enamels, nail polish removers, eyebrow pencils, blushers, eye creams, eye shadows, mascaras, eye liners, lip sticks, lip creams, shampoos, hair conditioners, hair colors, dispersion liquids, cleansing preparations, or the like.

Within the useful range of the active ingredients (GHG or GHG-containing composition) of this invention, the above items for skin care can be mixed with the ingredients of cosmetics or of quasi-drugs or the like, including e.g. oil, higher alcohol, fatty acids, ultraviolet absorbers, powders, pigments, surface-active agents, polyhydric alcohol and sugar, polymers, biologically active ingredients, solvents, antioxidants, aroma chemicals and antiseptics. These ingredients that are usable in the present invention are not limited to the examples described below.

(1) Specific Examples of Oil

Ester-Type Oil Phase Ingredient:

Glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, butyl myristate, ethyl linoleate, isopropyl linoleate, ethyl oleate, isocetyl myristate, isostearyl myristate, isostearyl palmitate, octyl dodecyl myristate, isocetyl isostearate, diethyl sebacate, diisopropyl adipate, isoaralkyl neopentanoate, glyceryl tri (caprylate/caprate), trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl myristate, isostearyl myristate, isocetyl palmitate, isostearyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol dioleate, propylene glycol dicaprate, propylene glycol dicaprylate/dicaprate), propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglyceryl oleate, polyglycerol Glycerin isostearate, dipropyl carbonate, dialkyl carbonate (C12-18), triisocetyl citrate, triisoaralkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di(2-ethylhexyl) succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearyl 12-stearoyl hydroxystearate, isostearyl 12-stearoyl hydroxystearate, or the like.

Hydrocarbon-Type Oil Phase Ingredient:

Squalene, liquid paraffin, α-olefin oligomer, isoparaffin, ceresin, paraffin, liquid isoparaffin, polybutene, microcrystalline wax, Vaseline, or the like.

Animal and Plant Oil, Hardened Oil Thereof, and Wax of Natural Origin:

Animal oils and hardened oils thereof, such as beef tallow, hardened beef tallow, lard, hardened lard, horse oil, hardened horse oil, mink oil, orange roughy oil, fish oil, hardened fish oil, egg yolk oil or the like; plant oils and hardened oils thereof such as avocado oil, almond oil, olive oil, cacao oil, kiwifruit seed oil, apricot kernel oil, kukui nut oil, sesame oil, wheat germ oil, rice germ oil, rice bran oil, safflower oil, shea butter, soybean oil, evening primrose oil, perilla oil, tea seed oil, tsubaki oil (camellia japonica oil), corn oil, rapeseed oil, hardened rapeseed oil, palm kernel oil, hardened palm kernel oil, palm oil, hardened palm oil, peanut oil, hardened peanut oil, castor oil, hydrogenated castor oil, sunflower oil, grape seed oil, jojoba oil, hardened jojoba oil, macadamia nut oil, meadowfoam seed oil, cottonseed oil, hardened cottonseed oil, coconut oil, hardened coconut oil, or the like; and waxes such as beeswax, high acid number beeswax, lanolin, reduced lanolin, hardened lanolin, liquid lanolin, carnauba wax and montan wax, or the like.

Silicone-Type Oil Phase Ingredient:

Dimethylpolysiloxane, methylphenyl-polysiloxane, methylcyclopolysiloxane, octamethylpolysiloxane, decamethylpolysiloxane, dodecamethylcyclosiloxane, methylhydrogenpolysiloxane, polyether-modified organopolysiloxane, dimethylsiloxane and methylcetyloxysiloxane Polymer, dimethylsiloxane/methylstearoxysiloxane copolymer, alkyl-modified organopolysiloxane, terminal-modified organopolysiloxane, amino-modified silicone oil, amino-modified organopolysiloxane, dimethiconol, silicone gel, acrylic silicone, trimethylsiloxysilicic acid, Silicone RTV rubber, or the like.

Fluorine-Type Oil Phase Ingredient:

Perfluoropolyether, fluorine-modified organopolysiloxane, pitch fluoride, fluorocarbon, fluoroalcohol, fluoroalkylipolyoxyalkylene co-modified organopolysiloxane, or the like.

(2) Specific Examples of Higher Alcohol

Lauryl alcohol, myristyl alcohol, cetyl alcohol, stearyl alcohol, isostearyl alcohol, oleyl alcohol, behenyl alcohol, 2-ethylhexanol, hexadecyl alcohol and octyl dodecanol, or the like.

(3) Specific Examples of Fatty Acids:

Caprylic acid, capric acid, undecylenic acid, lauric acid, myristic acid, palmitic acid, palmitoleic acid, stearic acid, isostearic acid, oleic acid, linoleic acid, linolenic acid, arachic acid, arachidonic acid, behenic acid, erucic acid, 2-ethylhexanoic acid, or the like.

(4) Specific Examples of Ultraviolet Absorber:

Para-aminobenzoic acid, amyl para-aminobenzoate, ethyldihydroxypropyl para-aminobenzoate, glyceryl para-aminobenzoate, ethyl para-aminobenzoate, octyl para-aminobenzoate, octyldimethyl para-aminobenzoate, ethylene glycol salicylate, octyl salicylate, triethanolamine salicylate, phenyl salicylate, butylphenyl salicylate, benzyl salicylate, homomenthyl salicylate, benzyl cinnamate, octyl para-methoxycinnamate, 2-ethylhexyl para-methoxycinnamate, glyceryl mono-2-ethyl hexanoate di-para-methoxycinnamate, isopropyl para-methoxycinnamate, diethanolamine para-methoxyhydrocinnamate, diisopropyl diisopropylcinnamic acid ester mixture, urocanic acid, ethyl urocanate, hydroxymethoxybenzophenone, hydroxymethoxybenzophenone sulfonic acid and a salt thereof, dihydroxymethoxybenzophenone, sodium dihydroxymethoxybenzophenonedisulfonate, dihydroxybenzophenone, dihydroxydimethoxybenzophenone, hydroxyoctoxybenzophenone, tetrahydroxybenzophenone, butylmethoxydibenzoylmethane, 2,4,6-trianilino-p-(carbo-2-ethylhexyl-1-oxy)-1,3,5-triazine, 2-(2-hydroxy-methylphenyl) benzotriazole, methyl-O-aminobenzoate, 2-ethylhexyl-2-cyano-3,3-diphenylacrylate, phenylbenzimidazole sulfuric acid, 3-(4-methylbenzylidene) camphor, isopropyldibenzoylmethane, 4-(3, 4-dimethoxyphenylmethylene)-2,5-doxy-1-imidazolidinepropionate, and polymer derivatives and silane derivatives thereof, or the like.

(5) Specific Examples of Powder and Pigment:

Pigments such as Food Red 104, Food Red 201, Food Yellow 4, Food Blue 1 and Food Black 401; lake pigments such as Food Yellow 4 AL lake and Food Yellow 203 BA lake; polymers such as nylon powder, silk powder, urethane powder, Teflon® powder, silicone powder, polymethyl methacrylate powder, cellulose powder, starch, silicone elastomer spherical powder and polyethylene powder; color pigments such as yellow iron oxide, red iron oxide, black iron oxide, chromium oxide, carbon black, ultramarine and iron blue; white pigments such as zinc oxide, titanium oxide and cerium oxide; extender pigments such as talc, mica, sericite, kaolin and plate barium sulfate; pearl pigments such as mica titanium; metal salts such as barium sulfate, calcium carbonate, magnesium carbonate, aluminum silicate and magnesium silicate; inorganic powders such as silica and alumina; metal soaps such as aluminum stearate, magnesium stearate, zinc palmitate, zinc myristate, magnesium myristate, zinc laurate and zinc undecylenate; bentonite; smectite; and boron nitride. The shape (e.g., sphere, bar, needle, plate, amorphous, scale, spindle) and the particle size of these powders are not particularly limited. These powders may or may not be previously surface-treated by a conventionally known surface treatment such as fluorine compound treatment, silicone treatment, silicone resin treatment, pendant treatment, saline coupling agent treatment, titanium coupling agent treatment, lubricant treatment, N-acylated lysine treatment, polyacrylic acid treatment, metal soap treatment, amino acid treatment, lecithin treatment, inorganic compound treatment, plasma treatment and mechanochemical treatment.

(6) Specific Examples of Surfactants

Anionic Surfactant:

Fatty-acid soap, a-acyl sulfonate, alkyl sulfonate, alkylallyl sulfonate, alkylnaphthalene sulfonate, alkyl sulfate, POE alkyl ether sulfate, alkylamide sulfate, alkyl phosphate, POE alkyl phosphate, alkylamide phosphate, alkyloylalkyl taurine salt, N-acylamino acid salt, POE alkyl ether carbonate, alkyl sulfosuccinate, sodium alkylsulfoacetate, acylated hydrolyzed collagen peptide salt, perfluoroalkylphosphoric acid ester, or the like.

Cationic Surfactant:

Alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, behenic acid amidopropyldimethyl hydroxypropylammonium chloride, diethylaminoethylamide stearate, dimethylaminoethylarnide stearate, dimethylaminopropylamide stearate, lanolin derivative quaternary ammonium salt, or the like.

Amphoteric Surfactant:

Carboxybetaine type, amidobetaine type, sulfobetaine type, hydroxysulfobetaine type, amidosulfobetaine type, phosphobetaine type, aminocarboxylate type, imidazoline derivative type, amidoamine type, or the like.

Nonionic Surfactant:

Propylene glycol fatty-acid ester, glycerin fatty-acid ester, polyglycerin fatty-acid ester, sorbitan fatty-acid ester, POE sorbitan fatty-acid ester, POE sorbitol fatty-acid ester, POE glycerin fatty-acid ester, POE alkyl ether, POE fatty-acid ester, POE hydrogenated castor oil, POE castor oil, POE-POP copolymer, POE-POP alkyl ether, polyether-modified silicone lauric acid alkanolamide, alkylamine oxide, hydrogenated soybean phospholipid, or the like.

Natural-Type Surfactant:

Lecithin, saponin, sugar-type surfactant, or the like.

(7) Specific Examples of Polyhydric Alcohol and Sugar

Ethylene glycol, diethylene glycol, polyethylene glycol, propylene glycol, dipropylene glycol, polypropylene glycol, glycerin, diglycerin, polyglycerin, 3-methyl-1,3-butanediol, 1,3-butylene glycol, sorbitol, mannitol, raffinose, erythritol, glucose, sucrose, fruit sugar, xylitol, lactose, maltose, maltitol, trehalose, alkylated trehalose, mixed isomerized sugar, sulfated trehalose, pullulan or the like. Chemically modified products thereof can also be used.

(8) Specific Examples of Polymer Compound

Anionic polymer compounds such as acrylic acid ester/methacrylic acid ester copolymer (PLUS-SIZE, produced by Sogokagaku K. K.), vinyl acetate/crotonic acid copolymer (Resin 28-1310, produced by NSC), vinyl acetate/crotonic acid/vinyl neodecanate copolymer (28-2930, produced by NSC), methyl vinyl ether maleic acid half ester (GANTREZ ES, produced by ISP), T-butyl acrylate/ethyl acrylate/methacrylic acid copolymer (RUBIMER, produced by BASF), vinylpyrrolidone/vinyl acetate/vinyl propionate copolymer (RUBISCOL VAP, produced by BASF), vinyl acetate/crotonic acid copolymer (RUBISET CA, produced by BASF), vinyl acetate/crotonic acid/vinylpyrrolidone copolymer (RUBISET CAP, produced by BASF), vinylpyrrolidone/acrylate copolymer (RUBIFLEX, produced by BASF), acrylate/acrylamide copolymer (ULTRAHOLD, produced by BASF), vinyl acetate/butyl maleate-isobornyl acrylate copolymer (ADVANTAGE, produced by ISP), carboxy vinyl polymer (CARBOPOL, produced by BF Goodrich) and acrylic acid-alkyl methacrylate copolymer (PAMUREN, produced by BF Goodrich); amphoteric polymer compounds such as acetic acid amphoteric compound of dialkylaminoethyl methacrylate polymer (YUKAFORMER, produced by Mitsubishi Chemical) and octylacrylamide acrylate/hydroxypropyl acrylate/butylarninoethyl methacrylate copolymer (AMPHOMER, produced by NSC); cationic polymer compounds such as quaternized compound of vinylpyrrolidone/dimethylaminoethyl methacrylate (GAFQUAT, produced by ISP) and methyl vinyl imidazolium chloride/vinylpyrrolidone copolymer (RUBICOTE, produced by BASF); and nonionic polymer compounds such as polyvinylpyrrolidone/vinyl acetate copolymer (RUBISCOL VA, produced by BASF) and vinylpyrrolidone/dimethylaminoethyl methacrylate copolymer (COPOLYMER VC713, produced by ISP).

In addition, polymer compounds of natural origin, such as cellulose and derivatives thereof, calcium alginate, pullulan, agar, gelatin, tamarind seed polysaccharides, xanthane gum, carrageenan, high-methoxyl pectin, low-methoxyl pectin, guar gum, gum arabic, crystal cellulose, arabino galactan, karaya gum, tragacanth gum, alginic acid, albumin, casein, cardrun, gellan gum, dextran or the like can also be suitably used.

(9) Specific Examples of Biologically Active Ingredients

The biologically active ingredient may include substances that are capable of imparting some biological activity to skin when such a substance is applied to the skin. Specific examples thereof may include: whitening ingredient, immunomodulator, age resistor, ultraviolet protection, slimming agent, skin tightening agent, antioxidant, hair restorer, hair growing agent, moisturizer, blood circulation accelerator, antibacterial agent, bactericide, desiccant, cooling agent, warming agent, vitamin compound, amino acid, wound healing accelerator, torpent, analgetic, cell activator and enzyme ingredient.

Suitable examples of the ingredient to be blended therefor may include: angelica extract, avocado extract, hydrangea extract, althea extract, arnica extract, aloe extract, apricot extract, apricot core extract, ginkgo extract, fennel extract, turmeric extract, oolong tea extract, rose fruit extract, echinacea leaf extract, scutellaria root extract, phellodendron bark extract, goldthread extract, barley extract, hypericum extract, white nettle extract, watercress extract, orange extract, sea salt, seaweed extract, hydrolyzed elastin, hydrolyzed wheat powder, hydrolyzed silk, chamomile extract, carrot extract, artemisia capillaris extract, glycyrrhiza extract, *Hibiscus sabdariffa* extract, pyracantha fortuneana fruit extract, cinchona extract, cucumber extract, guanosine, gardenia extract, sasa albo-marginata extract, sophora root extract, walnut extract, grapefruit extract, clematis extract, chlorella extract, mulberry bark extract, gentian extract, black tea extract, yeast extract, burdock extract, fermented rice bran extract, rice germ oil, comfrey extract, collagen, cowberry extract, asiasarum root extract, bupleurum falcatum root extract, umbilical cord extract, salvia extract, saponaria extract, bamboo grass extract, crataegus extract, zanthoxylum fruit extract, shiitake mushroom extract, rehmannia root extract, lithospermum root extract, perilla extract, linden extract, filipendula extract, peony root extract, calamus rhizome extract, birch extract, horsetail extract, ivy extract, hawthorn extract, sambucus nigra extract, yarrow extract, peppermint extract, sage extract, mallow extract, cnidium rhizome extract, swertia herb extract, soy extract, jujube extract, wild thyme extract, green tea extract, clove extract, cogon extract, citrus unshiu peel extract, angelica root extract, calendula extract, peach seed extract, bitter orange extract, houttuynia extract, tomato extract, natto extract, ginseng extract, garlic extract, wild rose extract, *hibiscus sabdariffa* flower extract, ophiopogon tuber extract, parsley extract, honey, witch hazel extract, pellitory extract, isodonis extract, matricaria extract, loquat extract, coltsfoot extract, butterbur scape extract, *Poria cocos* extract, butcher bloom extract, grape extract, propolis, luffa extract, safflower extract, peppermint extract, linden extract, peony extract, hop extract, pine extract, horse chestnut extract, skunk cabbage extract, sapindaceae extract, balm mint extract, peach extract, cornflower extract, eucalyptus extract, saxifrage extract, coix seed extract, mugwort extract, lavender extract, apple extract, lettuce extract, lemon extract, Chinese milk vetch extract, rose extract, rosemary extract, Roman chamomile extract, royal jelly extract, or the like.

Other examples may include biopolymers such as deoxyribonucleic acid, mucopolysaccharide, sodium hyaluronate, sodium, elastin, chitin, chitosan and hydrolyzed eggshell membrane; moisture retentive ingredients such as amino acid, hydrolyzed peptide, sodium lactate, urea, sodium pyrrolidonecarboxylate, betaine, whey and trimethylglycine; oily ingredients such as sphingolipid, ceramide, phytosphingosine, cholesterol, cholesterol derivatives and phospholipid; anti-inflammatory such as E-aminocaproic acid, glycyrrhizic acid, -glycyrrhetic acid, lysozyme chloride, guaiazlene and hydrocortisone; vitamins such as vitamin A, vitamin B2, vitamin B6, vitamin D, vitamin E, calcium pantothenate, biotin and nicotinic acid amide; active ingredients such as allantoin, diisopropylamine dichloroacetate and 4-aminomethylcyclohexanecarboxylic acid; antioxidants such as tocopherol, carotenoid, flavonoid, tannin, lignin and saponin; cell activators such as a-hydroxy acid and hydroxy acid; blood circulation accelerators such as y-orizanol and vitamin E derivatives; wound healing agents such as retinol and retinol derivatives; whitening agents such as albumin, kojic acid, placenta extract, sulfur, ellagic acid, linoleic acid, tranexamic acid and glutathione; and hair growing agents such as cepharanthine, glycyrrhiza extract, capsicum tincture, hinokitiol, iodized garlic extract, pyridoxine hydrochloride, DL-a-tocopherol, DL-a-tocopheryl acetate, nicotinic acid, nicotinic acid derivatives, calcium pantothenate, D-pantothenyl alcohol, acetyl pantothenylethyl ether, biotin, allantoin, isopropylmethylphenol, estradiol, ethynyl estradiol, capronium chloride, benzalkonium chloride, diphenhydramine hydrochloride, Takanal, camphor, salicylic acid, vanillylamide nonylate, vanillylamide nonanoate, pyroctone olamine, glyceryl pentadecanoate, L-menthol, mononitroguaiacol, resorcinol, y-aminobutyric acid, benzethonium chloride, mexiletine hydrochloride, auxin, female hormone, cantharis tincture, cyclosporine, zinc pyrithione, hydrocortisone, minoxidil, polyoxyethylene sorbitan monostearate, peppermint oil and SASANISHIKI extract, placenta products, *Citrus junos* seed extract, blueberry extract, lingonberry extract, *Cistanche tubulosa* extract, black rice extract, green coffee bean extract, resveratrol extract, kiwifruit seed extract, strawberry seed extract, cherry extract, or the like.

(10) Examples of Antioxidants

Plant extracts having an antioxidant effect, such as Sodium bisulfate, sodium sulfite, erythorbic acid, sodium erythorbate, dilauryl thiodipropionate, tocopherol, tolylbiguanide, nordihydroguaiaretic acid, parahydroxyanisole, butylhydroxyanisole, dibutylhydroxytoluene, ascorbyl stearate, palmitic acid, Ascorbyl, octyl gallate, propyl gallate, carotenoid, flavonoid, tannin, lignan, saponin, apple extract and clove extract, or the like.

The agent for improving the instantaneous force in the muscles of lower extremity and the agent for reducing muscle damage associated with intensive exercise of this invention are characterized by containing the above-mentioned purple-tea extract as an active ingredient. The purple-tea extract can be obtained by the same method as the aforementioned method for obtaining the GHG-containing composition, and also can be used for the composition in medicines (including pharmaceuticals and quasi-drugs), foods, drinks and cosmetics by the same method as the GHG-containing composition.

EXAMPLE

Hereinafter, a specific example of this invention is described, which is just one of many examples of this invention, and the scope of this invention is not limited just to this example.

Preparation of the Purple-Tea Extract (of the GHG-Containing Composition)

50 grams of Kenyan purple-tea leaf is immersed in 500 mL of a 50% aqueous solution of ethanol and then stirred and heated and refluxed at 40° C. for two hours until such solution becomes the extracted liquid. 400 mL of this extracted liquid is derived by suction-filtration. Such extracted liquid is then concentrated and dried into 16.6 grams of the purple-tea extract.

Isolation of GHG From Purple-Tea Extract

When the purple-tea extract was subjected to HPLC analysis under the following conditions, the peak of a component peculiar to the purple-tea extract, which is not contained in ordinary tea such as green tea, oolong tea, black tea or the like, was confirmed at 27.5 minutes (see the arrow in FIG. 1).

Preparation of samples: 350 mg of the purple-tea extract (GHG-content extract) was dissolved in a 30% methanol-aqueous solution, and the volume was fixed at 20 mL in the measuring flask. The solution was diluted and filtered twice and then analyzed by the HPLC.

The result of the HPLC analysis was as follows.

Condition of the HPLC analysis

Current speed: 0.7 mL/min

Mobile phase A: 0.3% TFA solution

Mobile phase B: Acetonitrile

Gradient: As shown in Table 1 below

Chromatography: SunFire C18, 4.6×150 mm (Waters) or equivalent

Chromatograph temperature: 30° C.

Sample injection volume: 10 µL

Detection wavelength: 280 nm

TABLE 1

| Time (in minutes) | Mobile-phase B concentration (%) |
|---|---|
| 0.0 | 5 |
| 4.0 | 5 |
| 4.5 | 10 |
| 27.0 | 15 |
| 47.0 | 55 |
| 48.0 | 90 |
| 50.0 | 90 |
| 51.0 | 5 |
| 60.0 | 5 |

The above components were separated and purified, and an NMR analysis was performed. The results, as seen in Table 2, show that one of the specific components, separated and purified, was identified as the known component 1,2-di-O-galloyl-4,6-O—(S)-hexahydroxydiphenyl-β-glucose (GHG).

TABLE 2

Chart 2. C-NMR Data of GHG of purple tea component

| Carbon No. | Purified component derived from purple tea | GHG literature value 1) |
|---|---|---|
| glucose | | |
| 1 | 94.4 | 94.4 |
| 2 | 74.6 | 74.7 |
| 3 | 74.1 | 74.1 |
| 4 | 73.1 | 73.1 |
| 5 | 73.8 | 73.8 |
| 6 | 64.1 | 64.1 |
| galloyl | | |
| 1 | 119.9 | 119.9 |
| 2.6 | 110.6 | 110.6 |
| 3.5 | 146.5 | 146.5 |
| 4 | 140.6 | 140.7 |
| 7 | 166.3 | 166.4 |
| 1' | 120.9 | 120.9 |
| 2'.6' | 110.4 | 110.5 |
| 3'.5' | 146.4 | 146.4 |
| 4' | 140.1 | 140.1 |
| 7' | 167.2 | 167.3 |
| HHDP | | |
| 1 | 116.9 | 116.9 |
| 2 | 126.2 | 126.2 |
| 3 | 108.6 | 108.7 |
| 4 | 145.9 | 145.9 |
| 5 | 137.7 | 137.7 |
| 6 | 144.9 | 144.9 |
| 7 | 169.4 | 169.4 |
| 1' | 116.6 | 116.6 |
| 2' | 126.5 | 126.5 |
| 3' | 108.4 | 108.5 |
| 4' | 145.8 | 145.8 |
| 5' | 137.4 | 137.4 |
| 6' | 144.8 | 144.8 |
| 7' | 169.8 | 189.9 |

1) Chem. Pharm. Bull. 57(11) 1284-1288 (2009)

The GHG-refined element is set as the standard substance of which a quantitative analysis was done by HPLC. The analysis showed that the purple-tea extract has a GHG of 8.70 percent by mass.

The purple-tea extract was separately prepared twice again in the same manner as described above, and the GHG content in the extract was measured by the same method. As a result, the GHG contents were 6.79% by mass and 6.38% by mass, respectively. Therefore, it was verified that the purple-tea extract, prepared according to the method of this invention, has a GHG of approximately 6-9% by mass.

Test Example 1: Evaluation of NO-Production-Promoting Activity of Purple-Tea Extract and of GHG The purple-tea sample and the GHG sample obtained in the above example were dissolved in a medium containing 1% DMSO (concentration: 10 to 1000 µg/mL) to prepare a sample solution. A medium containing 1% DMSO was used for a control.

Figure 2:
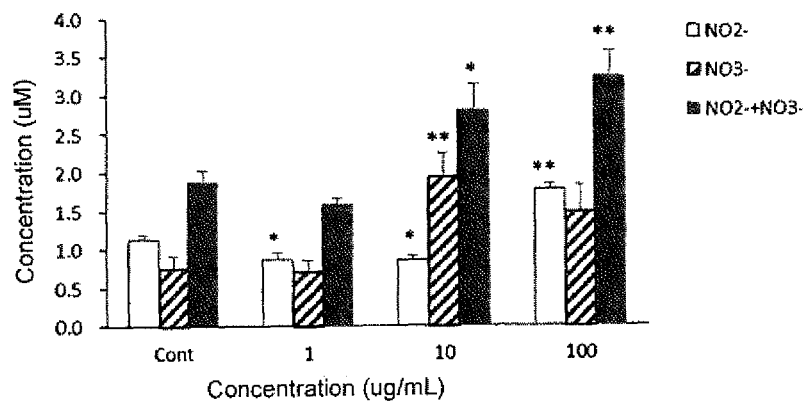
FIG. 2 is a graph showing the evaluation results of the NO-production promoting effect on the purple-tea extract.
Figure 3:
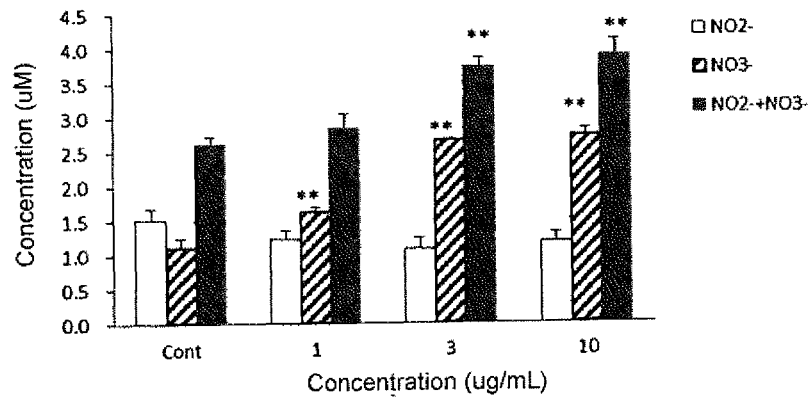
FIG. 3 is a graph showing the evaluation results of the NO-production promoting effect on the GHG.

Human umbilical vein endothelial cells (HUVEC) (6.2× 104 cells/500 µL) were seeded in 24-well plates, pre cultured for 1 day, then the medium was changed (450 µl). After that, a sample solution of 50 µL was added to each well to react for 24 hours. After the reaction, the culture supernatant was subjected to a measurement of a NO-production amount. For the measurement of the NO-production amount, "$NO_2/NO_3$ Assay Kit-FX" (trade name, manufactured by Dojindo Molecular Technologies, Inc.) was used. The results are shown in FIG. 2 (purple-tea extract) and FIG. 3 (GHG).

The $NO_2/NO_3$ Assay Kit-FX is a kit used for indirectly measuring NO in a sample by the fluorescence method, using the reaction between $NO_2^-$ and DAN (2,3-Diaminonaphthalene).

Results and Effects of Examples in Test Example 1

It was found that the purple-tea extract has a NO2-, NO3- and NO-total production effect. It was also found that the GHG has a NO3- and a NO-total production-promoting effect. From the above, it was confirmed that the purple-tea extract and the GHG are useful as NO-production promoters.

Test Example 2: Effect on Workout

Figure 4:
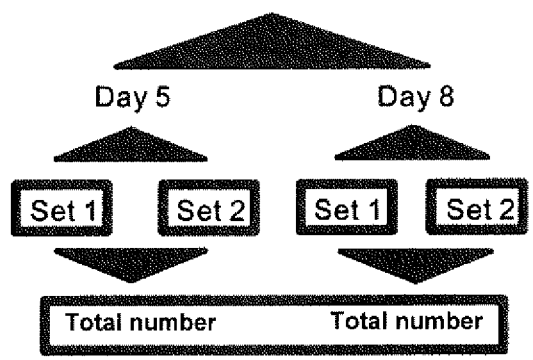
FIG. 4 is an explanatory diagram of the method for the exercise-effect test on the Kenyan purple-tea extract.
Figure 4:
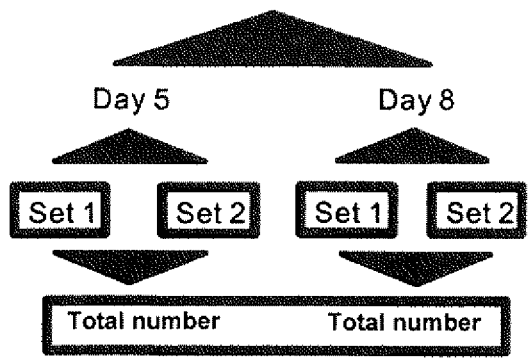

The test was done in a randomized placebo-controlled crossover format on 32 healthy American men undergoing resistance training once or twice a week. The average age of the men was 33.5 years, and their body weight and BMI were typical American figures. The men were subject to take placebo capsules or capsules containing purple-tea extract (100 mg) once daily in the morning. On the 5th and 8th days of ingestion, they were subject to carry out two sets each of bench presses (with a load equivalent to their body weight) and leg extensions (with a load equivalent to 50% of their body weight) up to the limit of their physical strength. After a two-week recovery period, the men were subject to take a different capsule than that which they had taken in the first half of the test. Then, a similar test was done. Blood was collected before and after exercise, and various parameters were measured (FIG. 4).

The results of the test are shown in Table 3 (exercise performance after administration), Table 4 (changes in muscle damage/inflammation markers) and Table 5 (degree of myoglobin and oxygen saturation after leg extension).

TABLE 3

Exercise performance after administration

| | Day 5 | Day 8 | Variation | p-value |
|---|---|---|---|---|
| Number of bench-presses - Set 1 | | | | |
| Placebo | 19.5 ± 8.6 | 20.0 ± 8.9 | 0.52 ± 1.7 | 0.46 |
| Purple-tea extract | 18.7 ± 7.7 | 19.6 ± 8.2 | 1.00 ± 2.8 | |
| Number of bench-presses - Set 2 | | | | |
| Placebo | 8.5 ± 3.3 | 8.6 ± 3.8 | 0.11 ± 1.9 | 0.75 |
| Purple-tea extract | 8.9 ± 4.0 | 9.2 ± 3.7 | 0.30 ± 1.8 | |
| Total number of bench-presses | | | | |
| Placebo | 28.0 ± 11.2 | 28.7 ± 12.3 | 0.63 ± 2.4 | 0.39 |
| Purple-tea extract | 27.6 ± 11.1 | 28.8 ± 11.2 | 1.28 ± 8.1 | |

TABLE 3-continued

Exercise performance after administration

| | Day 5 | Day 8 | Variation | p-value |
|---|---|---|---|---|
| Number of leg extensions - Set 1 | | | | |
| Placebo | 34.9 ± 13.8 | 35.8 ± 12.3 | 0.92 ± 7.2 | 0.05 |
| Purple Tea extract | 29.1 ± 8.0 | 33.7 ± 8.4 | 4.60 ± 4.4 | |
| Number of leg extensions - Set 2 | | | | |
| Placebo | 20.8 ± 4.2 | 21.4 ± 4.2 | 0.68 ± 3 1 | 0.80 |
| Purple-tea extract | 20.9 ± 5.6 | 21.8 ± 5.0 | 0.96 ± 3.7 | |
| Total number of leg extensions | | | | |
| Placebo | 55.7 ± 16.2 | 57.3 ± 15.5 | 1.60 ± 8.7 | 0.09 |
| Purple-tea extract | 50.0 ± 12.5 | 55.6 ± 12.7 | 5.56 ± 5.7 | |

Average value ± standard deviation

TABLE 4

Change in muscle damage/Inflammation marker

| | Day 5 | Day 8 | Variation | p-value |
|---|---|---|---|---|
| Creatin kinase | | | | |
| Placebo | 202 ± 267 | 262 ± 256 | 60.8 ± 288 | 0.98 |
| Purple-tea extract | 191 ± 137 | 250 ± 209 | 58.7 ± 193 | |
| LDH | | | | |
| Placebo | 170 ± 22 | 174 ± 28 | 4.8 ± 17.3 | 0.01 |
| Purple-tea extract | 175 ± 26 | 170 ± 28 | −5.5 ± 13.5 | |
| CRP | | | | |
| Placebo | 1.24 ± 1.41 | 1.21 ± 1.28 | −0.03 ± 0.79 | 0.66 |
| Purple-tea extract | 1.01 ± 0.94 | 1.09 ± 1.11 | 0.08 ± 0.71 | |

Average value ± standard deviation

TABLE 5

Myoglobin and oxygen saturation after the leg extensions

| | Myoglobin | | | | Oxygen saturation | | | |
|---|---|---|---|---|---|---|---|---|
| | Day 5 | p-value | Day 8 | p-value | Day 5 | p-value | Day 8 | p-value |
| Placebo | Before | | Before | | Before | | Before | |
| Purple-tea extract | loading | | loading | | loading | | loading | |
| | 12.4 ± 0.4 | | 12.5 ± 0.4 | | 52.6 ± 9.2 | | 55.0 ± 8.6 | |
| | 12.5 ± 0.4 | | 12.5 ± 0.4 | | 55. ± 8.5 | | 53.4 ± 7.9 | |
| Placebo | Immediately | 0.23 | Immediately | 0.24 | Immediately | 0.11 | Immediately | 0.61 |
| Purple-tea extract | after loading | | after loading | | after loading | | after loading | |
| | 12.6 ± 0.5 | | 12.6 ± 0.4 | | 14.6 ± 11.6 | | 16.0 ± 15.4 | |
| | 12.5 ± 0.5 | | 12.5 ± 0.4 | | 13.9 ± 8.8 | | 13.0 ± 10.2 | |
| Placebo | 30 sec. later | 0.48 | 30 sec. later | 0.53 | 30 sec. later | 0.04 | 30 sec. later | 0.71 |
| Purple-tea extract | 12.5 ± 0.4 | | 12.6 ± 0.4 | | 49.7 ± 17.1 | | 46.1 ± 17.2 | |
| | 12.5 ± 0.5 | | 12.5 ± 0.4 | | 45.6 ± 14.3 | | 43.4 ± 18.4 | |
| Placebo | 60 sec. later | 0.27 | 60 sec. later | 0.46 | 60 sec. later | 0.06 | 60 sec. later | 0.70 |
| Purple-tea extract | 12.5 ± 0.4 | | 12.5 ± 0.4 | | 67.5 ± 13.5 | | 64.8 ± 14.0 | |
| | 12.5 ± 0.4 | | 12.5 ± 0.4 | | 65.9 ± 10.3 | | 64.2 ± 17.5 | |

Results and Effects of Examples in Test Example 2

As a result of the test, there was no significant difference observed in the number of bench presses between the placebo group and the purple-tea group, but the number of successes of the first set of leg extensions was observed to have significantly increased in the purple-tea group on the 8th day of ingestion (Table 3). No increasing effect of the purple-tea extract was observed in the second set of leg extensions and in the total number of successes.

Regarding blood parameters, creatine kinase, having deviated from the skeletal muscles, increased in both groups from the 5th to 8th day of ingestion, but no suppression by the purple-tea extract was observed (Table 4). There was no change in the CRP of the inflammatory marker, but the LDH level, which had deviated due to cellular disorder, was significantly lower than that of the placebo group on the 8th day of ingestion of the purple-tea extract.

On the other hand, myoglobin, that is, a chromoprotein in muscle, hardly changed after the leg extensions (Table 5), but the degree of oxygen saturation on the 5th day of the administration was significantly lowered in the group of the purple-tea extract 30 seconds and 60 seconds after the leg extensions. From these results, it was clarified that purple-tea extract improves the performance of the muscles of the lower extremity, which requires instantaneous power at the start of training.

From this, it was confirmed that purple-tea extract is useful as an instantaneous-force-improving agent for the muscles of the lower extremity. At this time, it was observed that the LDH value in the blood decreases, confirming that the purple-tea extract reduced muscle damage associated with intensive exercise, thus considering purple-tea extract to be useful as a reducing agent for muscle damage associated with intensive exercise.

Examples of the NO-production promoter (i.e. the purple-tea extract of this invention), an enhancer of instantaneous force in the muscles of the lower extremity and a reducer of muscle damage associated with intensive exercise, which such promoter blended with the other substances, are described below. However, these examples are not limited.

Blending Example 1

| Chewing gums | |
|---|---|
| Sugar | 53.0 wt % |
| Gum base | 20.0 |
| Glucose | 10.0 |
| Starch syrup | 16.0 |
| Aroma chemical | 0.5 |
| Purple-tea extract | 0.5 |
| | 100.0 wt% |

Blending Example 2

| Gummies | |
|---|---|
| Reduction sugar | 40.0 wt % |
| Granulated sugar | 20.0 |
| Glucose | 20.0 |
| Gelatin | 4.7 |
| Water | 9.68 |
| Kiwi fruit juice | 4.0 |
| Kiwi fruit flavor | 0.6 |
| Pigment | 0.02 |
| Purle-tea extract | 1.0 |
| | 100.0 wt % |

Blending Example 3

| Candies | |
|---|---|
| Sugar | 50.0 wt % |
| Starch syrup | 33.0 |
| Water | 14.4 |
| Organic acid | 2.0 |
| Aroma chemical | 0.2 |
| Purole-tea extract | 0.4 |
| | 100.0 wt % |

Blending Example 4

| Yogurt (Hard type/Soft type) | |
|---|---|
| Milk | 41.5 wt % |
| Powdered skim milk | 5.8 |
| Sugar | 8.0 |
| Agar-agar | 0.15 |
| Gelatin | 0.1 |
| Lactic-acid bacterium | 0.005 |
| Purple-tea extract | 0.4 |
| Aroma chemical | a minute amount |
| Water | the rest |
| | 100.0 wt % |

Blending Example 5

| Soft drinks | |
|---|---|
| Fructose-glucose solution | 30.0 wt % |
| Emulsifying agent | 0.5 |
| Purple-tea extract | 0.05 |
| Aroma chemical | appropriate amount |
| Distilled water | the rest |
| | 100.0 wt % |

Blending Example 6

| Soft capsules | |
|---|---|
| Grape seed oil | 87.0 wt % |
| Emulsifying agent | 12.0 |
| Purple-tea extract | 1.0 |
| | 100.0 wt % |

Blending Example 7

| Tablets | |
| --- | --- |
| Lactose | 54.0 wt % |
| Crystalline cellulose | 30.0 |
| Starch-splitting product | 10.0 |
| Glycerin fatty-acid ester | 5.0 |
| Purple-tea extract | 1.0 |
| | 100.0 wt % |

Blending Example 8

| Oral-granule medicines (drugs and medicines) | |
| --- | --- |
| Purple-tea extract | 1.0 wt % |
| Lactose | 30.0 wt % |
| Corn starch | 60.0 |
| Crystalline cellulose | 8.0 |
| Polyvinylpyrrolidone | 1.0 |
| | 100.0 wt % |

Blending Example 9

TABLE t-shap

| Tablet-shaped sweets (drugs and medicines) | |
| --- | --- |
| Sugar | 76.4 wt % |
| Glucose | 19.0 |
| Sucrose-acid ester | 0.2 |
| Purple-tea extract | 0.5 |
| Distilled water | 3.9 |
| | 100.0 wt % |

Blending Example 15

| Cat foods | |
| --- | --- |
| Corn | 34.0 wt % |
| Wheat flour | 35.0 |
| Oatmeal | 15.0 |
| Beef fat | 8.9 |
| Salt | 1.0 |
| Bonito fish extract | 4.0 |
| Purple-tea extract | 1.0 |
| Taurine | 0.1 |
| Vitamins | 0.5 |
| Minerals | 0.5 |
| | 100.0 wt % |

Blending Example 16

| Dog foods | |
| --- | --- |
| Corn | 30.0 wt % |
| Meats (Chicken) | 15.0 |
| Defatted soybeans | 10.0 |
| Wheat flour | 25.0 |
| Chaff and bran | 5.0 |
| Purple-tea extract | 5.0 |
| Animal fat and oil | 8.9 |
| Oligosaccharide | 0.1 |
| Vitamins | 0.5 |
| Minerals | 0.5 |
| | 100.0 wt % |

INDUSTRIAL APPLICABILITY

As described above, this invention provides a NO-production promoter, an instantaneous-force-improving agent in the muscles of the lower extremity and a muscle-damage-reducing agent associated with intensive exercise, which is safe and has few side effects.

The invention claimed is:

1. A method for reducing muscle damage in a human being, comprising:
    a) providing an extract of Kenyan purple tea (scientific name: *Camellia sinensis*; variety name: TRFK306) containing 1,2-di-O-galloyl-4,6-O—(S)-hexahydroxy-diphenoyl-β-D-glucose (hereinafter referred to as GHG); and
    b) administering an effective amount of the purple-tea extract to a human being once a day for at least five days prior to the human being engaging in exercising, wherein the muscle damage associated with the exercising is reduced as determined by a reduced blood lactate dehydrogenase (LDH) level.

2. A method for reducing muscle damage in a human being according to claim 1, wherein the Kenyan purple tea extract contains 3 to 10% by mass of GHG.

* * * * *